United States Patent
Pinsonneault et al.

[11] Patent Number: 6,146,332
[45] Date of Patent: Nov. 14, 2000

[54] MOVEMENT DETECTOR

[75] Inventors: Maurice Pinsonneault, Knowlton, Canada; John Keith Millns, Romsey, United Kingdom

[73] Assignee: 3416704 Canada Inc., Québec, Canada

[21] Appl. No.: 09/124,117

[22] Filed: Jul. 29, 1998

[51] Int. Cl.[7] .............................. A61B 5/08; A61B 5/103
[52] U.S. Cl. ........................................ 600/534; 600/595
[58] Field of Search ................................ 600/534, 595, 600/552

[56] References Cited

U.S. PATENT DOCUMENTS

| Re. 32,180 | 6/1986 | Lewiner et al. | 600/534 |
|---|---|---|---|
| 4,509,527 | 4/1985 | Fraden | 600/534 |
| 4,657,026 | 4/1987 | Tagg | 600/534 |
| 5,235,989 | 8/1993 | Zomer | 600/534 |
| 5,271,412 | 12/1993 | Shtalryd et al. | 600/534 |
| 5,435,317 | 7/1995 | McMahon et al. | 600/534 |

FOREIGN PATENT DOCUMENTS 2192460  1/1998  United Kingdom .

*Primary Examiner*—Cary O'Connor
*Assistant Examiner*—Navin Natnithithadha
*Attorney, Agent, or Firm*—Swabey Ogilvy Renault; Guy J. Houle

[57] ABSTRACT

A movement detector for sensing movement from an infant lying on a mattress whether the infant is awake or asleep. The movement detector is comprised of a piezoelectric transducer secured between a pair of plates with a collector one of the plates having a bore or cavity configured in an inner flat surface thereof at the center of the plate, and with the backing plate of the transducer being secured about the cavity. A spacer element between the center of the transducer and the bottom plate, concentrates the movement forces on to the transducer. Electronic control circuits are provided to monitor the signals generated by the transducer to detect predetermined conditions of the signals in response to movement of the infant placed on the mattress.

13 Claims, 5 Drawing Sheets

MOVEMENT DETECTOR

TECHNICAL FIELD

The present invention relates to a detector responsive to movement, and more particularly but not exclusively, to the detection of the well-being of an infant positioned on a mattress.

BACKGROUND ART

Reference is made to U.K. Patent No. 2,192,460 issued to one of the inventors of the present application relating to a movement sensing detector of the type described herein. Although the sensor as described in the referenced patent works satisfactorily with certain European mattresses, it was found not to be sensitive enough when placed in the catchment area of much larger and thicker sprung mattresses to satisfactorily monitor the well-being of an infant present thereon while the infant is awake or sleeping. There is therefore the need to provide an improved more sensitive sensor capable of operating satisfactorily with larger foam and sprung mattresses.

Several years after the publication of the above referenced U.K. Patent, U.S. Pat. No. 5,271,412 was issued relating to a modified detector particularly useful for apnea (breathing) detection in infants to prevent sudden infant deaths which may occur while the infant is asleep. This improvement was constituted by mounting the electrode side of the piezoelectric transducer on an annular support ring disposed over the bottom plate. However, there are still several disadvantages associated with this modified design. One disadvantage is that the piezoelectric crystal is mounted in an inverted position as compared to the design which was proposed in U.K. Patent 2,192,460, which reduces its sensitivity. Another disadvantage is the assembly of the crystal at a precise location on the annular ring is also time consuming and the detector is more expensive to fabricate. A further disadvantage of this prior art design is that it is already significantly thicker than that proposed in U.K. Patent 2,192,460 and the annular spacer increases this, resulting in sensor pads that are bulky and often not fitting well under the mattress.

SUMMARY OF THE INVENTION

There is therefore a need to provide an improved movement detector using a piezoelectric crystal having its backplate mounted over a through bore or a cavity formed in the collector to provide a space within the collector for displacement of the crystal and thereby resulting in the fabrication of a thinner sensor pad.

Another feature of the present invention is to provide a movement detector having a piezoelectric crystal sensor and wherein the movement forces are concentrated on to the transducer via a spacer element mounted at the centre of the transducer.

Another feature of the present invention is to provide a movement detector using a piezoelectric crystal transducer and wherein the detector is simple and economical to fabricate and further wherein the collector and bottom plates as well as the separator support members can be molded from plastics material.

Another feature of the present invention is to provide a large movement detector of substantially, but not exclusively, rectangular configuration and wherein a single one of such detectors is necessary to detect the movement of an infant positioned on a mattress whether the infant is asleep or awake.

According to the above features, from a broad aspect, the present invention provides a movement detector which comprises a pair of flat plates of rigid material supported spaced apart by separator support members secured between the plates adjacent an outer circumferential edge of the plates. A piezoelectric transducer is secured between the plates substantially centrally thereof. The plates each define an outer and inner flat surface. The collector plate has a cavity configured in the inner flat surface thereof and substantially centrally thereof. The piezoelectric crystal transducer has an electrically-conductive backing plate disposed over and bridging a periphery of the cavity. The crystal is supported on the backing plate exteriorly of the cavity. An electrode film is secured in contact with the crystal. A fixed spacer element of semi-rigid material bridges an outer face portion of the electrode film and the inner flat surface of a supporting one of the plates for concentrating forces on the transducer. A pair of conductive wires are connected respectively to the backing plate and the electrode film whereby to generate electric signals when the plates flex with respect to one another by displacement of an exterior load positioned over the top plate. The conductor wires are connected to electric control circuit means to monitor the signals and to generate alarm signals upon detecting predetermined conditions of the signals.

BRIEF DESCRIPTION OF THE DRAWINGS

A preferred embodiment of the present invention will now be described with reference to the accompanying drawings in which.

DESCRIPTION OF PREFERRED EMBODIMENTS

Figure 1:
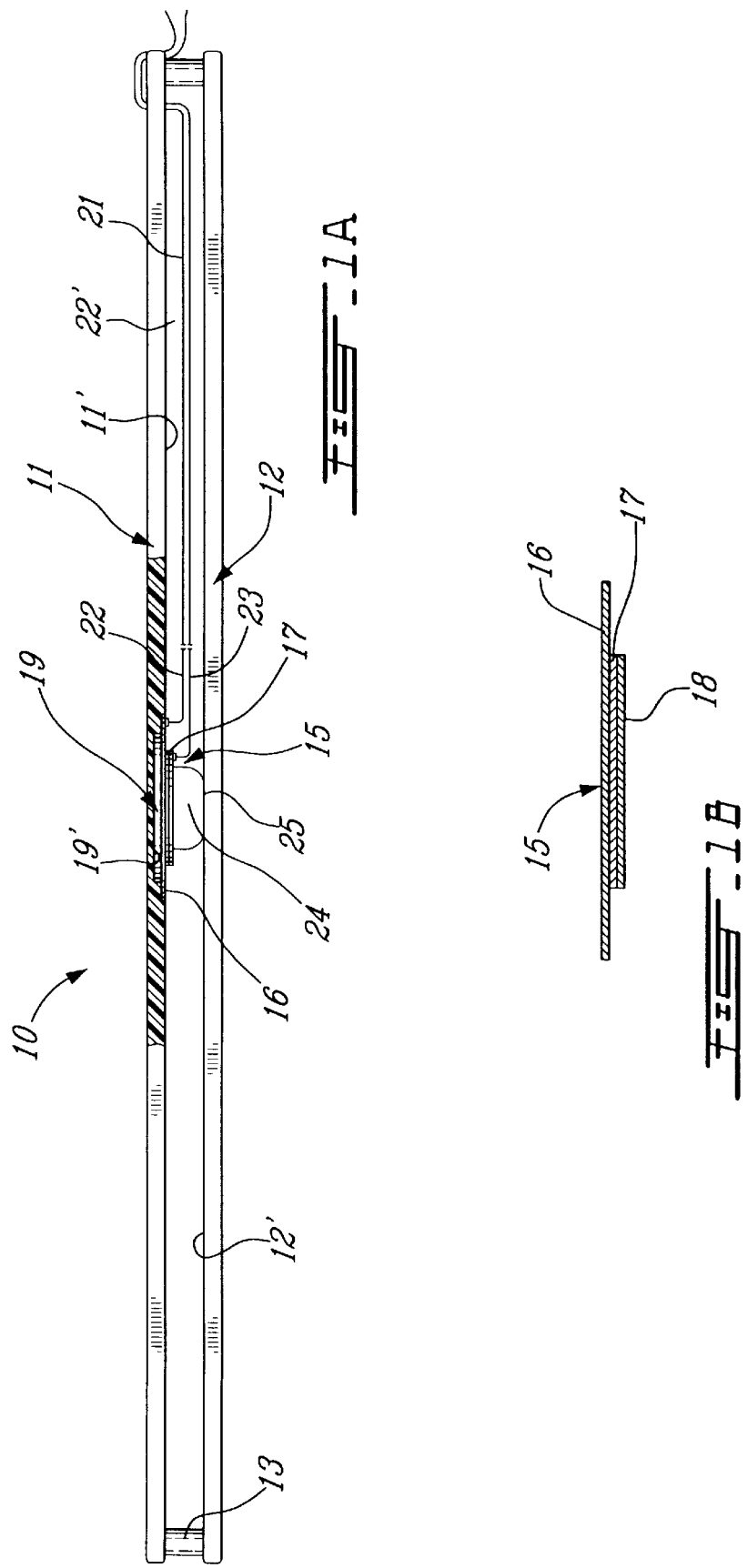
FIG. 1A is a side view partly sectioned illustrating the construction of the movement detector of the present invention.
FIG. 1B is a cross-section view of the piezoelectric crystal.
Figure 2:
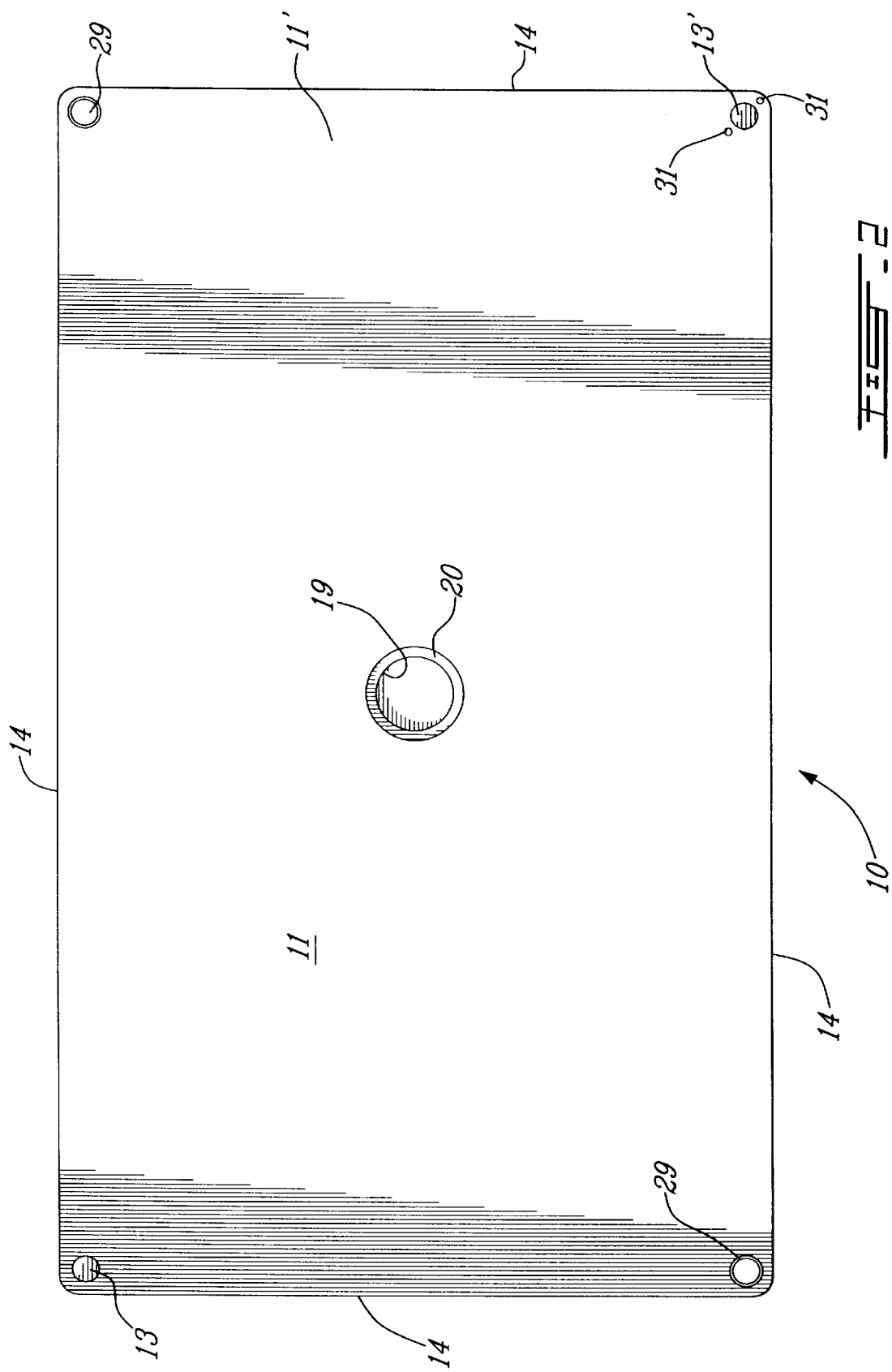
FIG. 2 is a top plan view of the inner face of the collector plate showing a through hole provided at the center of the plate and support posts and recesses formed in the corners of the inner face of the plate.
Figure 3:
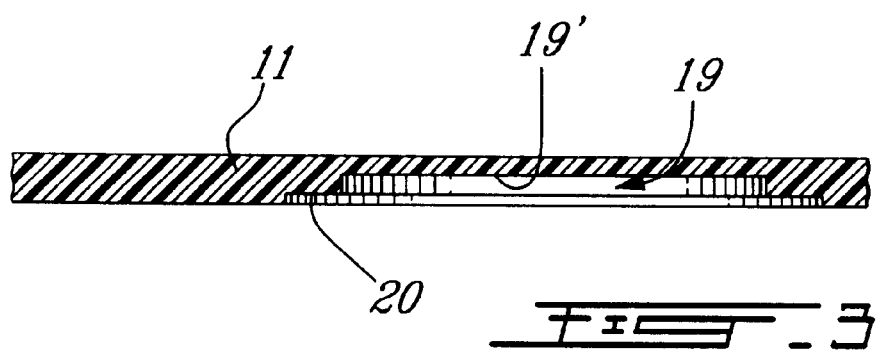
FIG. 3 is a section view illustrating a cavity and circumferential recess formed in the top collector plate in lieu of the through hole as shown in FIG. 2.

Referring now to the drawings, and more particularly to FIGS. 1 to 3, there is shown generally at 10 the movement detector of the present invention. It is comprised of a pair of flat rectangular plates, herein a collector plate 11 and a backing plate 12, molded from a semi-rigid plastics material and having a rectangular outline as shown in FIG. 2. The plates are supported spaced apart, as better shown in FIG. 1A by spacing support posts 13 secured adjacent the outer peripheral edges 14 and at the corners of the plates. These support posts 13 maintain the collector plate 11 and the backing plate 12 spaced apart in a substantially parallel relationship and at a predetermined distance from one another.

A piezoelectric transducer 15 is secured between the plates substantially centrally thereof. The transducer 15, as better shown in FIG. 1B, is comprised of an electrically-conductive backing plate 16 formed as a circular disc and having a crystal 17 supported thereon. An electrode film 18 is secured in contact with the outer face of the crystal 17.

As shown in FIGS. 2 and 3, a circular through bore at 19 may be formed in the backing plate substantially centrally thereof. Alternatively, a cavity may be formed instead, whereby to support the piezoelectric transducer thereover in the manner as illustrated in FIG. 1 and to permit excursion of the central portion of the crystal into the opening or cavity inside the collector plate. This permits the plates to be spaced closer to one another and thereby achieving a thinner sensing pad. Also, the back wall 19' of the cavity herein serves to limit the excursion or deflection of the transducer to prevent the crystal from cracking due to heavy loading. Although not illustrated, the sensor 10 may be disposed within a protective envelope.

Figure 5:
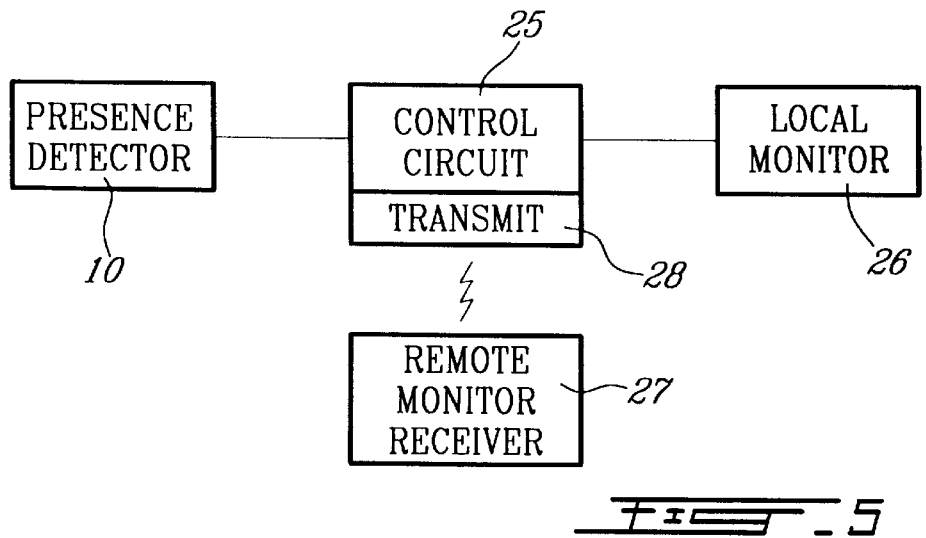
FIG. 5 is block diagram illustrating the arrangement of the electronic control circuits.

As shown in FIG. 1A, the backing plate 16 of the piezoelectric crystal is disposed concentrically over the cavity 19 which is herein a cavity of circular cross-section. The circular cavity or through bore may be provided with a recessed upper circumferential ledge 20 formed in the inner surface 11' of the collector plate whereby to precisely locate the circular backing plate 16 of the piezoelectric transducer therein. This backing plate is glued in the circumferential ledge 20. The recess also permits still further closer spacing of the plates. As shown in FIG. 1A, a two wire cable 21 extends within the area 22 between the plates 11 and 12 and has twin S leads. The first one of its leads 22 is connected to the backing plate 16 which is a brass plate. A second one of its leads, namely lead 23, is welded to the electrode film. A spacer element 24 of semi-rigid material, herein hard rubber, is required between the transducer and the bottom plate. This can be secured to the electrode film 17 by glue and positioned centrally thereon. The spacer 24 was first described in the above referenced U.K. Patent and is the key component in this and the above referenced U.S. patent. It should be noted that none of these sensor pad designs can function without it. In this embodiment, the spacer is provided with an outer flat face 25 for abutting relationship with the inner surface 12' of the backing plate. Accordingly, when a load is provided over the collector plate 11 and moved, the plates 11 and 12 will flex towards one another and the spacer element 24 will apply an upward pushing force onto the transducer causing the transducer to flex and generate an electric signal through the leads 22 and 23. This electric signal is sent to a control circuit 25, as schematically illustrated in FIG. 5. The electric signals are processed in the control circuit 25 and signals are transmitted to either a local alarm circuit 26 or a remote receiver 27 through a transmitter 28. Alarms are generated upon detecting predetermined signal conditions. The control circuit will not be described as such is known in the art and described in U.K. Patent 2,192,460, as mentioned herein above.

Figure 4A:
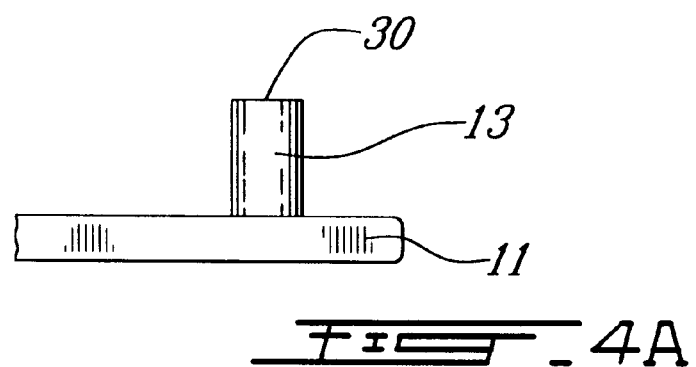
FIG. 4A is a side view showing the construction of the support posts formed integrally with the collector and backing plates.
Figure 4B:
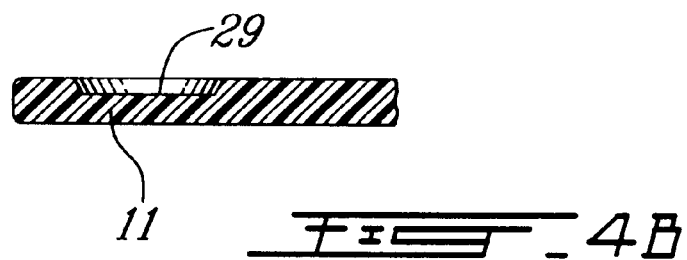
FIG. 4B is a section view showing the configuration of the recess formed integrally with the collector and backing plates.

As shown in FIGS. 4A and 4B when the collector plate and bottom plates are molded, they are each molded with diagonally-opposed support posts 13 and diagonally-opposed recesses 29 for receiving the top portion 30 of the support posts 13 of the other plate, therein. These spacer posts may be glued within the recesses 29 or fused therein.

As shown in FIG. 2, holes 31 may be provided adjacent one of the posts 13' for the passage of the cable 21 thereto in a U-shaped fashion to prevent any exterior pulling force on the cable being transmitted to the twin leads 22 and 23.

Figure 6:
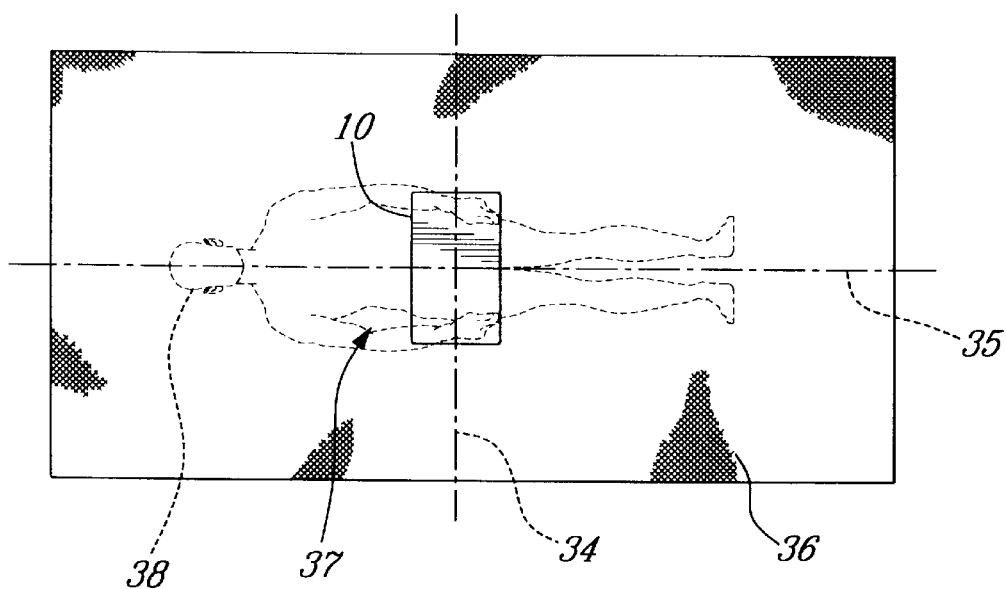
FIG. 6 is a top view showing the location of the movement detector with respect to a mattress.
Figure 8:
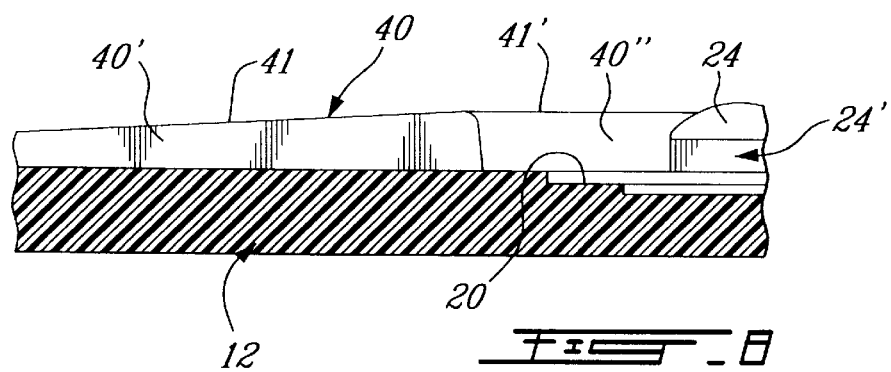
FIG. 8 is a fragmented sectional side view showing the shape of the reinforcing ribs projecting from the inner face of the bottom backing plate and the centre spacer subassembly.

As shown in FIG. 6, the detector 10 of the present invention is preferably located with its longitudinal axis 34 oriented transverse to the longitudinal axis 35 of a mattress 36 and in the area 37 immediately under an infant 38 positioned on the mattress 36. The sensor has a high degree of sensitivity sufficient to detect the body movement of an infant caused by respiratory motion. Accordingly, the monitor can be said to detect apnea in infants in order to sound an alarm to minimize the possibility of sudden infant death while the infant is asleep. The reason why it is preferred to locate the movement detector at right angles to the longitudinal axis of the mattress is that infants have more of a tendency to move sideways while sleeping rather than up or down the bed. A theoretical improvement in the sensitive 'catchment' area is described in the referenced U.S. patent where two sensor pads are used and connected in parallel (one placed at the top of the bed and the other nearer the bottom). However, in practice it has been found that this can produce null positions where opposite polarity signals from both pads cancel. It can be appreciated that with the construction of the movement detector as herein described, the detector is very simple to assemble and the piezoelectric transducer is precisely positioned with respect to the through hole or cavity 18 or 19, particularly when a circumferential ledge 20 is provided about the through hole or cavity. The cavity and ledge also permit the construction of a thinner detector pad. Also, by having the hard rubber disc spacer 24 glued onto the opposed surface of the piezoelectric wafer, there is no need to provide precise alignment between the collector plate and the bottom plate whereby to locate the spacer centrally on the wafer. However, the corner support posts in FIG. 4, positively locate the collector and bottom plates, this allows part of the spacer 24' to be fabricated from the hard plastic material and fixed to the bottom plate as shown in FIG. 8. In this case, it is important to ensure that the tip of the spacer 24 is a semi-rigid material, such as rubber, to prevent damage to the electrode film of the transducer.

Figure 7:
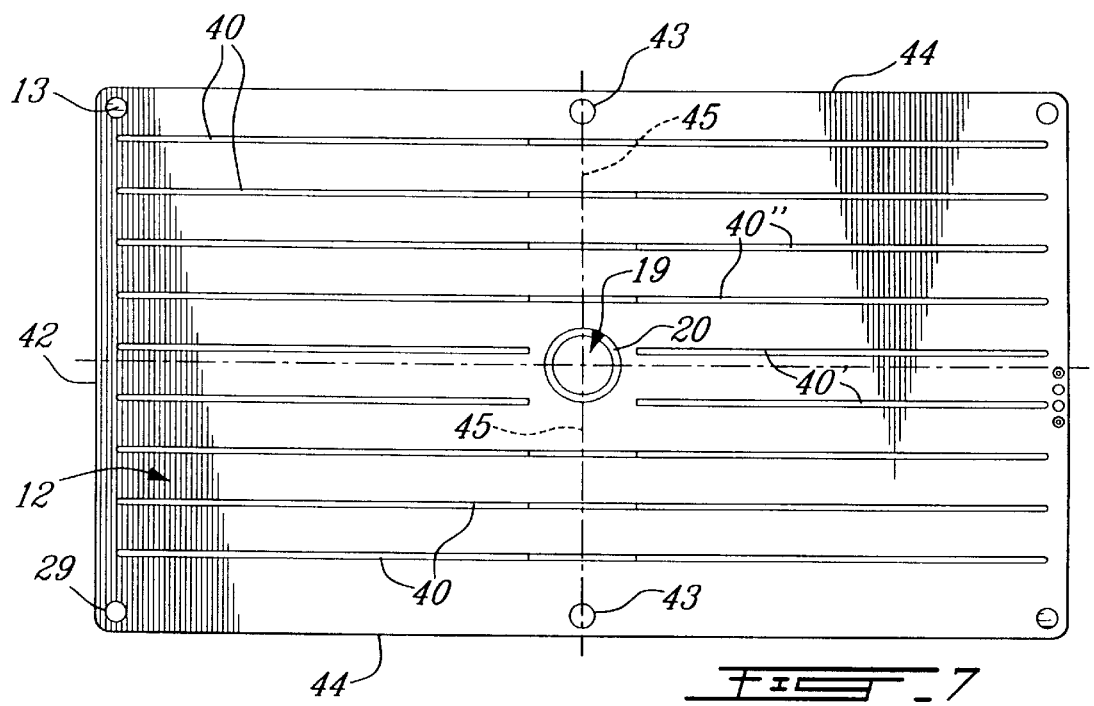
FIG. 7 is a plan view showing a modification to the inner face of the collector plate.
Figure 9:
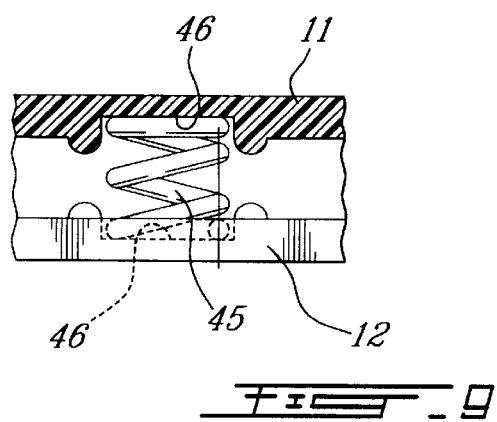
FIG. 9 is a partly fragmented section view of the spring supports.

Referring now to FIGS. 7 to 9, and particularly to FIG. 7, there is shown at 11 the collector plate having the cavity 19 located centrally thereof with its circumferential ledge 20. It has been found that in order to add rigidity to the collector plate as well as to the bottom plate 12, it is preferable to provide reinforcing ribs 40 at spaced apart intervals therealong. The ribs from the bottom plate would be offset from the ribs of the collector plate, that is to say, they would fall in between one another in alignment. Accordingly, the ribs would not interfere from one another and as can be seen from FIG. 8 the spacer 24 projects above these ribs so as to be in contact with the collector plate, as previously described. These reinforcing ribs 40 are provided with a tapered outer edge 41 tapering to the outer end edges 42 of the collector plate. The ribs 40' in the area adjacent the transducer 15 terminate short of that area whereas the outside ribs such as 40" are formed with a flat top edge 41' as shown in FIG. 8 whereby the plates can flex towards one another to permit the plate displacement to be sensed by the piezoelectric 15 through the spacer element 24.

As shown in FIGS. 7 and 9, in order to maintain the plates substantially in parallel planes and because these plates are provided with support posts 13 only in the corners thereof, an improvement of the movement detector resides in the provision of resilient supports at other locations, in particular, at 43 adjacent the opposed longitudinal side edges 44 of the collector plate as well as the bottom plate and along the central transverse sections 45 of the detector. These resilient supports can be made from a variety of materials and small metal helical compression springs 45 were found to be ideal. These are retained captive within opposed recesses 46 and 46' provided in the collector plate 11 as well as the bottom plate 12, as shown in FIG. 9. These compression springs 45 have a selected compression strength sufficient to maintain the plates spaced apart but permitting the plates to flex towards one another for sensing the displacement of a load position above a mattress or any other medium disposed on top of the detector.

Those skilled in the art will appreciate that the conception, upon which this disclosure is based, may readily be utilized as a basis for the designing of other structures, for carrying out the several purposes of the present invention. It is important, therefore, that the claims be regarded as including such equivalent constructions insofar as they do not depart from the spirit and scope of the present invention.

What is claimed is:

1. A movement detector comprising a pair of flat plates of semi-rigid material supported spaced apart by separator support members secured between said plates adjacent an outer circumferential edge of said plates, a piezoelectric compression transducer secured between said plates substantially centrally thereof, said plates each defining an outer and inner flat surface, a collector one of said plates having a cavity configured in said inner flat surface thereof substantially centrally thereof, said piezoelectric crystal transducer having an electrically conductive backing plate disposed over and bridging a periphery of said cavity, a crystal supported on said backing plate exteriorly of said cavity, an electrode film secured in contact with said crystal, a spacer element of semi-rigid material bridging an outer face portion of said electrode film and said inner flat surface of a supporting one of said plates for concentrating forces on said transducer, a pair of conductor wires connected respectively to said backing plate and said electrode film whereby to generate electric signals when said plates flex with respect to one another by displacement of an exterior load positioned over said top plate, said conductor wires being connected to electronic control circuit means to monitor said signals and to generate alarm signals upon detecting predetermined conditions of said signals, said collector plate and said supporting plate being molded of semi-rigid plastic material, said separator support members being corner posts molded with at least one of said plates and connected to the other of said plates to maintain said plates positively secured in close spaced apart registry with one another, and reinforcing ribs formed integral with said collector plate and supporting plate and protecting from an inner surface of said plates.

2. A movement detector as claimed in claim 1 wherein said cavity is a circular cavity, said backing plate of said transducer being in the form of a thin circular plate.

3. A movement detector as claimed in claim 2 wherein said thin circular plate is a metal plate.

4. A movement detector as claimed in claim 2 wherein said circular cavity is provided with a recessed upper circumferential ledge dimensioned to receive an outer peripheral portion of said circular plate in close contact therein to minimize possible damage to said transducer from excessive deflection from heavy loads.

5. A movement detector as claimed in claim 1 wherein said cavity is formed by a through hole in said collector plate.

6. A movement detector as claimed in claim 5 wherein said through hole is of circular cross section.

7. A movement detector as claimed in claim 1 wherein said detector is adapted to be interposed under a sleeping mattress for monitoring displacement of an infant positioned on said mattress when said infant is sleeping or awake.

8. A movement detector as claimed in claim 7 wherein said detector is a respiration monitor having a sensitivity sufficient to monitor movement of an infant occasioned by respiration of said infant.

9. A movement detector as claimed in claim 7 wherein said plates are rectangular plates interconnected in close spaced apart registry, said detector being positioned under said sleeping mattress with the longitudinal axis of said rectangular plates oriented transverse to the longitudinal axis of said mattress, and substantially under an area where an infant is to be positioned on said mattress.

10. A movement detector as claimed in claim 7 wherein said spacer element is fixedly attached to said outer face of said electrode film to prevent wear of said electrode film, said spacer element having an outer flat contact surface for contact with said inner flat surface of said bottom plate.

11. A movement detector as claimed in claim 7 wherein said spacer element is attached to the bottom plate, said spacer element having a tip end in contact with the transducer, at least said tip end being of a semi-rigid material, such as rubber, to prevent damage to the electrode film of the transducer.

12. A movement detector as claimed in claim 1 wherein said ribs are elongated parallel spaced apart ribs which taper from a central region of said plates to outer end edges of said plates, said ribs in said bottom plate being offset from said ribs in said collector plate.

13. A movement detector comprising a pair of flat plates of semi-rigid material supported spaced apart by separator support members secured between said plates adjacent an outer circumferential edge of said plates, a piezoelectric compression transducer secured between said plates substantially centrally thereof, said plates each defining an outer and inner flat surface, a collector one of said plates having a cavity configured in said inner flat surface thereof substantially centrally thereof, said piezoelectric crystal transducer having an electrically conductive backing plate disposed over and bridging a periphery of said cavity, a crystal supported on said backing plate exteriorly of said cavity, an electrode film secured in contact with said crystal, a spacer element of semi-rigid material bridging an outer face portion of said electrode film and said inner flat surface of a supporting one of said plates for concentrating forces on said transducer, a pair of conductor wires connected respectively to said backing plate and said electrode film whereby to generate electric signals when said plates flex with respect to one another by displacement of an exterior load positioned over said top plate, said conductor wires being connected to electronic control circuit means to monitor said signals and to generate alarm signals upon detecting predetermined conditions of said signals, there being further provided a pair of compression springs, each spring of said pair being retained captive between said collector and bottom plates adjacent an outer side edge of said plates and aligned with a central transverse straight axis passing through said transducer to maintain said plates spaced apart while permitting said plates to move towards one another in the area of said transducer.

* * * * *